United States Patent [19]

Suzukamo et al.

[11] Patent Number: 4,473,703

[45] Date of Patent: Sep. 25, 1984

[54] METHOD OF EPIMERIZATION OF ALKYL CHRYSANTHEMATE

[75] Inventors: Gohfu Suzukamo, Osaka; Masami Fukao, Shiga, both of Japan

[73] Assignee: Sumitomo Chemical Company, Limited, Osaka, Japan

[21] Appl. No.: 359,319

[22] Filed: Mar. 18, 1982

[30] Foreign Application Priority Data

Mar. 30, 1981 [JP] Japan ................................. 56-47817
Apr. 24, 1981 [JP] Japan ................................. 56-62714

[51] Int. Cl.$^3$ .......................................... C07C 67/333
[52] U.S. Cl. ................................. 560/124; 562/506
[58] Field of Search ........................ 560/124; 562/506

[56] References Cited

U.S. PATENT DOCUMENTS

| | | | |
|---|---|---|---|
| 3,046,299 | 7/1962 | Julia ................................. | 560/124 |
| 3,538,143 | 11/1970 | Matsui ................................. | 560/124 |
| 3,794,680 | 2/1974 | Matsui et al. ........................ | 260/514 |
| 3,906,026 | 9/1975 | Nagase et al. ....................... | 560/124 |
| 3,931,280 | 1/1976 | Nagase ................................. | 560/124 |
| 3,989,750 | 11/1976 | Nagase et al. ....................... | 260/544 |
| 4,008,268 | 2/1977 | Mizutoni ............................. | 562/506 |
| 4,182,906 | 1/1980 | Suzukamo et al. ................... | 562/506 |

FOREIGN PATENT DOCUMENTS

47-26778 7/1972 Japan .
49-126650 12/1974 Japan .................................. 562/506

OTHER PUBLICATIONS

Williams et al., Tetrahedron Letters, vol. 22, pp. 385–388 (1981).
Hanafusa et al., Chemistry and Industry, pp. 1050–1051 (1970).

*Primary Examiner*—Michael L. Shippen
*Attorney, Agent, or Firm*—Birch, Stewart, Kolasch & Birch

[57] ABSTRACT

A process for isomerization of cis-chrysanthemate esters by contacting a chrysanthemate ester containing a cis-chrysanthemate ester with a Lewis acid, to transform the cis-chrysanthemate ester into trans-chrysanthemate ester through epimerization at $C_3$-position. The starting cis-chrysanthemate ester may be of any optical isomer ratio form (+)-form to (−)-form, including racemic form. Accordingly the process is effectively employable for the preparation of a (+)-trans-chrysanthemate ester from the (+)-cis-chrysanthemate ester. Combinations of the process with optical resolution would make the commercial production of (+)-trans-chrysanthemic acid more effective, the latter being an important acid component of pyrethroidal insecticides.

12 Claims, No Drawings

METHOD OF EPIMERIZATION OF ALKYL CHRYSANTHEMATE

The present invention pertains to a method for isomerization of cis-chrysanthemate esters. More particularly, it pertains to a process for isomerization of alkyl or cycloalkyl cis-chrysanthemate esters (hereinafter referred to "cis-ester") through epimerization at the $C_3$-position, which comprises contacting an alkyl or cycloalkyl chrysanthemate ester containing the "cis-ester", alone or in combination with the corresponding trans-chrysanthemate ester, with a Lewis acid, to transform the "cis-ester" into the corresponding trans-chrysanthemate ester to obtain an alkyl or cycloalkyl trans-chrysanthemate ester (hereinafter referred to "trans-ester"), or an alkyl or cycloalkyl chrysanthemate ester rich in the "trans-ester".

As the most particular aspect, the present invention relates to a process for isomerizing optically active "cisesters", which comprises contacting an optically active "cis-ester", represented by the formula (I),

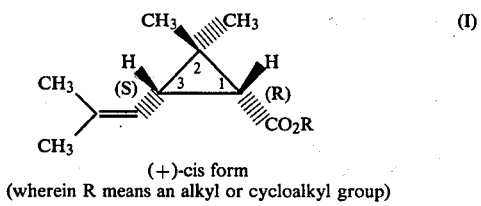

(+)-cis form
(wherein R means an alkyl or cycloalkyl group)

or an alkyl or cycloalkyl chrysanthemate ester rich in (+)-"cis-ester" with a Lewis acid, to transform the optically active "cis-ester" into the optically active "trans-ester" represented by the formula (II),

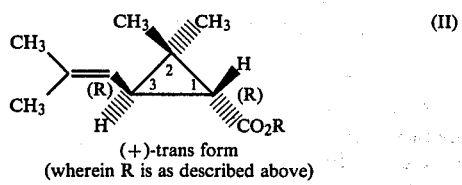

(+)-trans form
(wherein R is as described above)

to obtain the (+)-"trans-ester", or an alkyl or cycloalkyl chrysanthemate ester rich in (+)-"trans-ester".

Thus, the object of present invention is to provide a process for the transformation of the configuration at the $C_3$-position of an alkyl or cycloalkyl chrysanthemate, in other words, a process for the isomerization based upon the $C_3$-epimerization.

Chrysanthemic acid is the acid component of the esters known as so-called "pyrethroidal insecticides" such as pyrethrin, allethrin, phthalthrin, etc.

This carboxylic acid has four optical isomers, that is, two geometrical isomers (cis and trans forms), each of which has two optical isomers [(+)- and (−)-forms]. In general, among these four isomers of pyrethroidal esters, it has been known that trans form esters possess stronger activity than cis form esters, and the (+)-form exhibits much higher effectiveness than the corresponding (−)-form. Also, optically active trans-chrisanthemic acid is useful as a resolving agent for optically active amines.

As illustrated above, chrysanthemic acid possesses two assymmetric carbons at $C_1$- and $C_3$-positions, and the four isomers, (+)-cis, (−)-cis, (+)-trans and (−)-trans forms, have the absolute configuration of (1R, 3S,) (1S, 3R), (1R, 3R) and (1S, 3S), respectively. As for the isomerization process of chrysanthemic acid compounds, processes of the transformation of $C_1$-configuration, namely the $C_1$-epimerization, have already been known. For example, a process in which an alkyl cischrysanthemate is treated with a specific base catalyst (Japanese Published Examined Patent application Nos. 18495/1978 and 18496/1978), and a process in which pyrethric acid chloride is heated at a high temperature (Japanese Published Examined Patent application No. 24694/1971), have been proposed. All of these are for the transformation of $C_1$-configuration. And in these processes, when (+)-cis-chrysanthemic acid compound is employed as the starting material, (−)-trans-isomer is obtained, which exhibits little insecticidal effectiveness as the pyrethroidal esters.

Also, a process has been known in which a chrysanthemic acid halide of any of four isomers is contacted with a Lewis acid to transform the same into the racemate, namely (±)-form (U.S. Pat. Nos. 3989750 and 4182906). According to the process, any of four isomers can be racemized and particularly, an advantage of the process is that (−)-trans form compound can be racemized. However, the (+)-cis compound is racemized into (±)-trans compound, in this process.

As mentioned above, there have already been known several processes for epimerization at the $C_1$-position and racemization of chrysanthemic acid compounds. However, a process to prepare the trans form compound through the transformation of $C_3$-configuration ($C_3$-epimerization) has not previously been known. Thus, there has never been an effective process to obtain the (+)-trans form compound from the (+)-cis isomer.

It has now been found that (+)-cis chrysanthemic acid compounds can be transformed into (+)-trans compounds through the $C_3$-epimerization efficiently under comparatively moderate reaction conditions, by contacting the (+)-cis carboxylic acid ester with a Lewis acid. The present invention is based on such findings with additional studies.

The relationship of the transformation with respect to the present invention may be illustrated according to the following diagram.

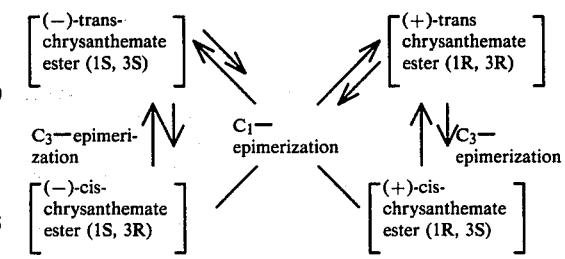

The alkyl or cycloalkyl chrysanthemate obtained according to the present invention can be converted easily to chrysanthemic acid by hydrolysis. The starting optically active cis-chrysanthemate esters can be prepared by a process of the optical resolution of (±)-cis chrysanthemic acid, followed by the esterification (Japanese Published Unexamined Patent application No. 125342/1974), or by a process to derive it from an optically active dihydrochrysanthemolactone (Japanese Published Unexamined Patent Application No. 30669/1972, etc.). Accordingly, any combination of these technologies with the process of the present invention enables the obtainment of the (+)-trans form compound with high efficiency.

As is clear from the above diagram, when (−)-"cis-ester" is employed as the starting material in this invention, (−)-"trans-ester" can be obtained. The thus obtained (−)-"trans-ester" is converted easily to (−)-trans-chrysanthemic acid which is useful as a resolving agent.

Also, in the case where a racemic "cis-ester" is employed as the starting material, the racemic "trans-ester" can be prepared. Accordingly, the process of the present invention is to provides a novel process to prepare a racemic "transester" from the racemic "cis-ester" or its cis-trans mixture.

Moreover, in case where a "cis-ester" having any optical purity, namely (+)-dominant cis or (−)-dominant cis isomers is employed as the starting material, the trans-chrysanthemate ester having the same sign of optical rotation can be prepared according to the present invention.

The process according to the present invention will more concretely be described below. An alkyl or cycloalkyl chrysanthemate containing a "cis-ester" is contacted with a Lewis acid particularly metal halide type Lewis acid, such as boron trifluoride-etherate, iron chloride, aluminum chloride, aluminum bromide, titanium chloride, zinc chloride, etc., and the complex compounds thereof, to readily effect $C_3$-epimerization, irrespective of the external pressure, thereby to transform the "cis-ester" to a "trans-ester".

In the case where the optically active cis-chrysanthemate esters are employed as the starting material, they may be of solely the cis form or a mixture in any proportion with the transchrysanthemate ester having the same sign of optical rotation. Further, they may be of any degree of optical purity, or any optical isomer ratio, including racemic form. It is preferable to employ the optically active ester having exclusively or dominantly one side of the optical rotations, from the standpoint of the utilization of the product.

In the present invention, the substituent R in the esters as represented in the formulae (I) and (II), may be an alkyl or cycloalkyl group having 1 to 10 carbon atoms, including methyl, ethyl, propyl, butyl, hexyl, octyl, menthyl, etc. group.

In carrying out the process of the present invention, a solvent is preferably used, which does not essentially obstruct the reaction. As such solvent, there may be illustrated saturated hydrocarbon, including hexane, heptane, cyclohexane, octane, etc., halogenated aromatic hydrocarbon, including chlorobenzene, etc., and ethers. Among them, hexane, heptane and other saturated hydrocarbons are preferred.

The amount of Lewis acid employed is not particularly limitative, but may ordinarily be within the range from about 1/200 mol to the equivalent mol, preferably from about 1/100 to ½ mol, based on the mol of the ester material.

The reaction temperature may ordinarily be selected from the range of about −70° to 150° C., preferably from about −30° to 100° C., since an exceedingly high temperature tends to cause cleavage of the cyclopropane ring or other side reactions.

The reaction time varies depending upon the amount of Lewis acid employed and the reaction temperature. Usually the isomerization is accomplished within about 1 minute to 20 hours. The proceeding of the reaction can be checked by any of gas-chromatography, liquid chromatography, measurement of the optical rotation, etc. The process of the present invention may be carried out under a diminished or pressurized atmosphere, but easily under the ordinary atmosphere, to fulfill the present object. To ensure the present process, it is more preferable to carry out the process in an inert gas atmosphere, such as nitrogen.

To practice the process of the present invention, any of batchwise and continuous procedures are embployed. As the mode of feeding the materials, any methods can be employed, for example, the starting ester and a Lewis acid may be added into a reaction vessel, or the ester or the Lewis acid may be continuously or intermittently added depending upon the proceeding of the reaction.

After completion of the reaction, the reaction mixture may be treated to remove the Lewis acid, and concentrated to obtain an optically active "trans-ester" or a chrysanthemate ester mainly comprising the same. Hydrolysis of the resulting ester with an aqueous alkali solution, readily gives optically active trans-chrysanthemic acid or chrysanthemic acid mainly comprising the same, which may be further purified by distillation or a chromatography.

The optically active chrysanthemic acid thus obtained may be utilized for various usages. For example, (+)-trans-chrysanthemic acid can be converted to various highly effective insecticidal compounds, by the reaction with a group of alcohol, so-called pyrethroidal alcohols, such as pyrethrolone, allethrolone, etc.

The present invention will be further illustrated in the following Examples, which however, should never be construed to be limitative.

EXAMPLE 1

To a mixture of 4.0 g of ethyl (+)-cis-chrysanthemate and 100 ml of n-heptane, placed in a 200 ml flask under nitrogen atmosphere, was added 1.36 g of aluminum chloride. The mixture was stirred at a temperature of 70° C. for 3 hours. Thereafter, water was added to the reaction mixture to decompose and separate the aluminum chloride. The organic layer was washed with water and concentrated to obtain 4.0 g of the residue.

Its infrared spectrum showed the coincidence to that of ethyl trans-chrysanthemate.

Distillation of the residue yielded 3.5 g of an oily product boiling at 106° to 116° C./20 mmHg.

The product was mixed with 6.2 g of an aqueous 20% sodium hydroxide solution, and the mixture was stirred at a temperature of 100° C. for 2.5 hours to effect hydrolysis. The reaction mixture was extracted with toluene to remove the neutral substance, and the aqueous layer was acidified with a diluted hydrochloric acid. The isolated acid, weighing 2.4 was a trans-rich chrysanthemic acid having the composition of 88.4% of (+)-trans, 1.1% of (−)-trans, and 10.5% of (+)-cis-isomer by weight (analyzed by gas chromatography).

EXAMPLE 2

In a 100 ml flask, 2.0 g of an ethyl chrysanthemate having the optical isomer ratio of 3.6% of (−)-cis, 19.1% of (+)-cis, 10.5% of (−)-trans and 66.9% of (+)-trans forms by weight, was dissolved into 18.0 g of n-heptane under nitrogen. To the solution was added 0.7 g of aluminum chloride, and the mixture was stirred at a temperature of 70° C. for 3 hours. Thereafter, water was added to the reaction mixture to decompose the aluminum chloride. The organic layer separated was evaporated to remove the solvent, and the residue was mixed with 6.1 g of an aqueous 10% sodium hydroxide solution and stirred at a temperature of 100° C. for 2.5 hours to effect the hydrolysis. The reaction mixture was extracted with toluene to separate the neutral substance. The aqueous layer was acidified with a diluted sulfuric acid and then extracted with toluene. The toluene layer was washed with water, dried and evaporated to remove the solvent. Distillation in vacuo yielded 1.32 g of a trans-chrysanthemic acid boiling at 110° to 116° C./2 mmHg. Its analysis by gas-chromatography showed the optical isomer ratio of 0.9% of (−)-cis, 6.3% of (+)-cis, 12.4% of (−)-trans and 80.4% of (+)-trans forms by weight.

EXAMPLES 3–6

Using various alkyl esters of the chrysanthemic acid as shown in the following table, having the same isomer ratio as that used in Example 2, the reactions of the present process were carried out under the conditions as identified in the table, with the results as shown therein.

TABLE

| Example | Chrysanthemate esters used (g) | Solvent (g) | Lewis acid (g) | Reaction condition temp. (°C.) | Reaction condition time | Yield of chrysanthemic acid produced (%) | Final optical isomer ratio (wt. %) (−)-cis | (+)-cis | (−)-trans | (+)-trans |
|---|---|---|---|---|---|---|---|---|---|---|
| 3 | ethyl ester (2.0) | n-heptane (18.0) | FeCl$_3$ (0.65) | 70 | 3 hours | 75.1 | 0.7 | 4.9 | 6.0 | 88.4 |
| 4 | methyl ester (1.8) | n-heptane (16.2) | BF$_3$—ether complex (0.57) | 50 | 30 minutes | 88.0 | 0.6 | 4.8 | 13.7 | 81.0 |
| 5 | n-butyl ester (2.2) | n-heptane (19.8) | AlCl$_3$ (0.5) | 70 | 3 hours | 92.0 | 1.6 | 15.4 | 10.9 | 72.2 |
| 6 | ethyl ester (2.1) | n-heptane (50.0) | AlCl$_3$ (1.0) | 70 | 3 hours | 76.7 | 0.9 | 6.1 | 16.8 | 76.2 |

*Optical isomer ratio of chrysanthemic acid esters used:
(−)-cis: 3.6%
(+)-cis: 19.1%
(−)-trans: 10.5%
(+)-trans: 66.9%

EXAMPLE 7

Into a mixture of 4.0 g of racemic ethyl chrysanthemate and 100 g of n-heptane, placed in a 200 ml flask under nitrogen, was added 1.36 g of aluminum chloride. The resulting mixture was stirred at a temperature of 70° C. for 3 hours for reaction. Water was added to the reaction mixture to decompose and remove the aluminum chloride. The organic layer was washed with water, and then concentrated to give 4.0 g of a reaction product. Distillation of the product yielded 3.4 g of an oily distillate boiling at 110° to 116° C./21 mmHg. Its infrared spectrum coincided to that of racemic ethyl trans-chrysanthemate. The ester was mixed with 6.2 g of an aqueous 20% sodium hydroxide solution, and the mixture was stirred at a temperature of 100° C. for 2.5 hours to effect hydrolysis. Toluene was added to the hydrolysate to extract the neutral substance. The aqueous layer was acidified with a diluted sulfuric acid, and the isolated substance was extracted with toluene. The toluene layer was washed with water and then concentrated to give 2.4 g of racemic trans-rich chrysanthemic acid. A gaschromatography analysis showed the isomeric ratio of 12% of cis and 88% of trans forms.

EXAMPLE 8

Into a mixture of 2.0 g of racemic ethyl chrysanthemate composed of 34.1% of cis and 65.9% of trans by weight, and 18.0 g of n-heptane, placed in a 100 ml flask under nitrogen was added 0.7 g of aluminum chloride. The resulting mixture was stirred at a temperature of 70° C. for 3 hours. After the reaction, water was added to the reaction mixture to decompose and remove the aluminum chloride. After removal of the solvent, the residue was mixed with 3.1 g of an aqueous 20% sodium hydroxide solution, and the mixture was heated at a temperature of 80° to 100° C. for 3 hours to effect hydrolysis. The reaction mixture was extracted with toluene to remove the neutral substance, and the aqueous layer was acidified with a diluted sulfuric acid and extracted with toluene. The toluene layer was washed with water, dried, concentrated and distilled to give 1.3 g of trans-rich chrysanthemic acid boiling at 109° to 116° C./2 mmHg.

A gas-chromatography analysis showed its isomeric ratio of 8.1% of cis and 91.9% of trans forms by weight.

EXAMPLE 9

Into a mixture of 2.0 g of racemic ethyl chrysanthemate employed in Example 8 and 18.0 g of n-heptane, placed in a 100 ml flask under nitrogen was added 0.65 g of iron(III) chloride. The resulting mixture was stirred at a temperature of 70° C. for 3 hours.

After the reaction, water was added to the reaction mixture to decompose and remove the iron(III) chloride. The organic layer was concentrated to leave 1.5 g of racemic ethyl chrysanthemate. A gas-chromatography analysis of the ester showed the isomeric ratio of 6.2% of cis and 93.8% of trans forms by weight.

EXAMPLE 10

Similarly as in Example 9, a mixture of 2.0 g of ethyl chrysanthemate, 18.0 g of n-heptane and 0.43 g of boron trifluoride-ether complex was stirred at a temperature of 50° C. for 0.5 hour. The reaction mixture was treated as mentioned above, to give 1.76 g of ethyl chrysanthemate having the isomeric ratio of 5.9% of cis and 94.1% of trans forms by weight.

EXAMPLE 11

Similarly as in Example 9, a mixture of 2.0 g of methyl chrysanthemate (34.8% of cis and 65.2% of trans forms), 18.0 g of n-heptane and 0.59 g of aluminum chloride was stirred at a temperature of 70° C. for 1 hour. The reaction mixture was treated as mentioned above, to give 1.4 g of methyl chrysanthemate having the isomeric ratio of 7.7% of cis and 92.3% of trans forms by weight.

EXAMPLE 12

Similarly as in Example 9, a mixture of 2.0 g of n-butyl chrysanthemate (34.5% of cis and 65.5% of trans), 18.0 g of n-heptane and 0.48 g of aluminum chloride was stirred at a temperature of 70° C. for 3 hours. The reaction mixture was treated as mentioned above, to give 1.6 g of n-butyl chrysanthemate having the isomeric ratio of 13.9% of cis and 86.1% of trans forms by weight.

EXAMPLE 13

Similarly as in Example 9, a mixture of 2.0 g of ethyl chrysanthemate (same as in Example 9), 18.0 g of n-heptane and 0.14 g of aluminum chloride was allowed to react at a temperature of 70° C. for 3 hours. The reaction mixture was treated as mentioned above, to give 1.8 g of ethyl chrysanthemate having the isomeric ratio of 12.7% of cis and 87.3% of trans forms by weight.

We claim:

1. A process for isomerizing optically active alkyl or cycloalkyl cis-chrysanthemates, which comprises contacting an optically active alkyl or cycloalkyl chrysanthemate containing an optically active alkyl or cycloalkyl cis-chrysanthemate, alone or in a combination with the corresponding trans-isomer, with a Lewis acid selected from the group consisting of boron trifluoride-etherate, iron chloride, aluminum chloride, aluminum bromide, titanium chloride, zinc chloride and complex compounds thereof, to transform the alkyl or cycloalkyl cis-chrysanthemate into the corresponding trans-chrysanthemate by epimerization at the $C_3$-position to obtain an optically active alkyl or cycloalkyl trans-chrysanthemate or an alkyl or cyclo-alkyl chrysanthemate rich in an optically active trans form ester.

2. A process for isomerizing optically active alkyl or cycloalkyl cis-chrysanthemates, which comprises contacting an optically active alkyl or cycloalkyl chrysanthemate or an alkyl or cycloalkyl chrysanthemate rich in an optically active alkyl or cycloalkyl cis-chrysanthemate, the said optically active chrysanthemate having any optical isomer ratio of (+)-cis and (−)-cis form, with a Lewis acid selected from the group consisting of boron trifluoride-etherate, iron chloride, aluminum chloride, aluminum bromide, titanium chloride, zinc chloride and complex compounds thereof, to transform the alkyl or cycloalkyl cis-chrysanthemate into the alkyl or cycloalkyl trans-chrysanthemate having substantially the same sign of optical rotation to obtain an optically active alkyl or cycloalkyl trans-chrysanthemate or an alkyl or cycloalkyl chrysanthemate rich in an optically active alkyl or cycloalkyl trans-chrysanthemate.

3. A process according to claim 2, wherein the optically active alkyl or cycloalkyl cis-chrysanthemate is the alkyl or cycloalkyl (+)-cis-chrysanthemate.

4. A process according to any of claims 1, 2 or 3, wherein the alkyl or cycloalkyl is the alkyl or cycloalkyl group having 1 to 10 carbon atoms.

5. A process according to claim 4, wherein the alkyl or cycloalkyl is selected from the group consisting of methyl, ethyl, propyl, hexyl, octyl and menthyl.

6. A process according to any one of Claims 1, 2 and 3, wherein the contact of the alkyl or cycloalkyl cis-chrysanthemate to the Lewis acid is effected in a solvent selected from the group consisting of saturated hydrocarbon, halogenated aromatic hydrocarbon and ethers.

7. A process according to claim 6, wherein the contact of the alkyl or cycloalkyl cis-chrysanthemate to the Lewis acid is effected in a solvent selected from the group consisting of hexane, heptane, cyclohexane, octane and chlorobenzene.

8. A process according to any one of claims 1, 2 or 3, wherein the amount of the Lewis acid employed is within the range from about 1/200 mol to the equivalent mol based on the mol of the ester material.

9. A process according to any one of claims 1, 2 or 3, wherein the reaction is effected at a temperature of from about −70° C. to 150° C.

10. A process according to claim 9, wherein the reaction is effected at a temperature of from −30° C. to 100° C.

11. A process according to claim 1, wherein the alkyl or cycloalkyl is selected from the group consisting of methyl, ethyl, propyl, hexyl, octyl and menthyl.

12. A process for isomerizing optically active alkyl or cycloalkyl cis-chrysanthemates, which comprises contacting an optically active alkyl or cycloalkyl chrysanthemate rich in an optically active alkyl or cycloalkyl (+)-cis-chrysanthemate, alone or in combination with the corresponding trans-isomer, with a Lewis acid selected from the group consisting of boron trifluoride-etherate, iron chloride, aluminum chloride, aluminum bromide, titanium chloride, zinc chloride and complex compounds thereof, to transform the alkyl or cycloalkyl (+)-cis-chrysanthemate into the corresponding (+)-trans-chrysanthemate by epimerization at the $C_3$-position to obtain an optically active alkyl or cycloalkyl trans-chrysanthemate or an alkyl or cycloalkyl chrysanthemate rich in an optically active (+)-trans form ester.

* * * * *